(12) United States Patent
Yelvington et al.

(10) Patent No.: US 10,352,865 B1
(45) Date of Patent: Jul. 16, 2019

(54) FLUID FLOW CELL AND METHOD FOR PHOTOMETRIC ANALYSIS

(71) Applicants: Paul E. Yelvington, Rockledge, FL (US); Andrew L. Carpenter, Rockledge, FL (US); Andrew L. Wagner, Cocoa Beach, FL (US)

(72) Inventors: Paul E. Yelvington, Rockledge, FL (US); Andrew L. Carpenter, Rockledge, FL (US); Andrew L. Wagner, Cocoa Beach, FL (US)

(73) Assignee: MAINSTREAM ENGINEERING CORPORATION, Rockledge, FL (US)

( * ) Notice: Subject to any disclaimer, the term of this patent is extended or adjusted under 35 U.S.C. 154(b) by 225 days.

(21) Appl. No.: 15/486,698

(22) Filed: Apr. 13, 2017

(51) Int. Cl.
*G01N 21/85* (2006.01)
*G01N 21/59* (2006.01)
*G01N 21/05* (2006.01)
*G01N 21/47* (2006.01)

(52) U.S. Cl.
CPC ............ *G01N 21/85* (2013.01); *G01N 21/05* (2013.01); *G01N 21/47* (2013.01); *G01N 21/59* (2013.01); *G01N 2021/4709* (2013.01); *G01N 2201/08* (2013.01)

(58) Field of Classification Search
CPC .... G01N 33/2888; G01N 21/85; G01N 21/05; G01N 2201/08; G01J 3/42
See application file for complete search history.

(56) References Cited

U.S. PATENT DOCUMENTS

| 2,212,211 | A | | 8/1940 | Pfund |
|---|---|---|---|---|
| 3,734,601 | A | | 5/1973 | Heiss |
| 4,637,730 | A | | 1/1987 | Fonslingl et al. |
| 4,786,171 | A | | 11/1988 | LeFebre et al. |
| 5,046,854 | A | | 9/1991 | Weller et al. |
| 5,054,869 | A | | 10/1991 | Doyle |
| 5,065,025 | A | | 11/1991 | Doyle |
| 5,120,129 | A | | 6/1992 | Farquharson et al. |
| 5,241,368 | A | | 8/1993 | Ponstingl et al. |
| 5,340,987 | A | | 8/1994 | Eckles et al. |
| 5,408,313 | A | | 4/1995 | Ponstingl et al. |
| 5,610,400 | A | | 3/1997 | Weckström |
| 5,616,923 | A | * | 4/1997 | Rich ................. G01N 21/0303 250/338.5 |
| RE36,489 | E | | 1/2000 | Alexay |
| 6,734,961 | B2 | | 5/2004 | Gerner et al. |
| 6,867,857 | B2 | | 3/2005 | Hobbs |

(Continued)

FOREIGN PATENT DOCUMENTS

| EP | 0597152 A1 | 5/1994 |
|---|---|---|
| EP | 0670486 A1 | 9/1995 |
| WO | WO 2005047869 A1 | 5/2005 |

*Primary Examiner* — Maurice C Smith
(74) *Attorney, Agent, or Firm* — Michael W. O'Neill, Esq.

(57) ABSTRACT

A flow cell and method for photometric transmission measurements are disclosed in which a folded optical path provides for co-located, collinear fiber optic read and illumination cables that can be bundled together. Light passes through a fluid sample, is reflected off a pair of right-angle turning mirrors and returns through the fluid for a second pass. A center divider separates fluid passages on the first pass of the light through the fluid and the second pass of the light through the fluid to block any undesired backscattered light from reaching a detector.

20 Claims, 5 Drawing Sheets

(56) References Cited

U.S. PATENT DOCUMENTS

| | | | |
|---|---|---|---|
| 7,339,657 B2 * | 3/2008 | Coates | G01N 21/31 |
| | | | 250/339.12 |
| 7,382,458 B2 | 6/2008 | Johnson et al. | |
| 7,446,317 B2 | 11/2008 | Doyle | |
| 8,842,282 B2 | 9/2014 | Keller et al. | |
| 2005/0175273 A1 * | 8/2005 | Iida | B01L 3/502715 |
| | | | 385/15 |
| 2009/0051901 A1 * | 2/2009 | Shen | B29D 11/00365 |
| | | | 356/73 |
| 2009/0279072 A1 * | 11/2009 | Arakawa | G01N 21/314 |
| | | | 356/70 |
| 2010/0288941 A1 * | 11/2010 | Ayliffe | B01L 3/0217 |
| | | | 250/432 R |
| 2011/0262307 A1 * | 10/2011 | Packirisamy | G01N 21/05 |
| | | | 422/82.08 |
| 2013/0250303 A1 * | 9/2013 | Shirata | B25J 9/102 |
| | | | 356/436 |
| 2016/0161335 A1 * | 6/2016 | Doyle | G01J 3/0218 |
| | | | 250/227.23 |

* cited by examiner

FLUID FLOW CELL AND METHOD FOR PHOTOMETRIC ANALYSIS

STATEMENT REGARDING FEDERALLY SPONSORED RESEARCH OR DEVELOPMENT

This invention was made with Government support under contract W911QX-13-C-0005 awarded by the U.S. Army. The Government has certain rights in the invention.

BACKGROUND AND SUMMARY OF THE INVENTION

The present invention is concerned with an improved apparatus and method for photometric analysis of fluid samples and the like. More particularly, the present invention is concerned with a sample cell and method for photometric analysis of fluid flows.

As is well known, photometric analysis provides information on the chemical composition of a sample fluid. In many different industrial processes, such as petroleum refineries, pharmaceutical plants, chemical plants, wastewater plants and the like, measuring the chemical composition of a fluid stream is beneficial for the purpose of characterizing the properties of that stream for quality assurance or process control. Photometric analysis can also be used on power plants, fuel cells, or propulsion engines to characterize the fuel and lubrication oil for the purpose of detecting contaminants, wear debris, or thermal degradation.

In a flowing system, such as a chemical process, wastewater treatment plant, combustion engine or the like, the fluid is exposed for measurement in a flow cell or sample cell having windows to allow the transmittance of light from a light source to a detector. The present invention, generally speaking, is directed towards such a flow cell in which fiber optic ports allow attachment of flexible fiber optic cables. In such a flow cell, an illumination cable carries light from the light source such as a laser, light emitting diode, or a broadband lamp to the flow cell, and a read cable carries light from the flow cell to the a detector such as a photodetector or spectrometer. Attenuation of the transmitted light is caused by absorption or scattering of light by the fluid or by particles suspended in the fluid, as the fluid passes through the flow cell which has an inlet and outlet connection for the flowing fluid.

Probes are also used for photometric analysis of fluids, either in a tank vessel or a pipe. Distinct from the flow cell, a probe is inserted into a measurement port, usually a threaded bung, on the vessel or pipe. Probes can measure transmission in a so-called transflectance probe or transmission dip probe, or measure attenuated total reflectance, or measure Raman scattering. Transflectance probes have a cylindrical probe body with an open cavity in the tip of the body that allows fluid to pass through the measurement location. The light traverses through the cavity and is reflected off an angled mirror onto an optic element, such as a lens or read fiber. In addition to the transmitted light that is attenuated due to absorbance, the read-optic also receives backscattered light from the fluid and any suspended particles in the fluid. This backscattered light causes measurement noise, decreases the signal-to-noise ratio, and leads to an ill-defined optical path length. Transmission flow cells do not suffer from backscattering. As a result, transmission flow cells have better optical signal performance than transflectance probes. However, transflectance probes have the advantage that they package nicely because the read- and illumination-fiber can be bundled together in birfurcated fiber optic cable.

Flow cells commonly have a cross configuration where the optical ports are on opposite sides and the fluid ports are also on opposite sides, thereby forming a cross. A disadvantage of cross flow cells is that the fiber optic cables are on opposite sides of the flow cell. Because the fiber optic cables have a large minimum bend radius to avoid breaking the fiber, the cables must form excessively large loops before being bundled together and running to the photodetector and light source. Often times the minimum bend radius is 4 to 8 inches, which commonly is substantially larger than the flow cell to which the cables are connected. The large looping fiber optics are a significant limitation for measurement applications where packaging is tight and space is constrained such as in a vehicle or aircraft. The fiber optic cables are fragile, and the end terminations of the cable are often a failure point. In addition, the loops in the cables provide a risk of snagging and thereby damaging the cable. Other known approaches use a folded optical configuration similar to the transflectance probe that positions the optical connections on the same face of the flow cell; however, these flow cells also suffer from backscattering like the transflectance probes.

The present invention deals with a flow cell and method for transmission measurements in fluid that address the foregoing problems and shortcomings of known approaches. Our flow cell includes a folded optical path that provides for co-located, collinear fiber optic cables. The light passes through the sample, is reflected off a pair of turning mirrors and returns through the fluid for a second pass. As such the read and illumination cables can be bundled together, greatly easing the packaging constraints inherent with fiber optic cables. Unlike known folded optical path flow cells, the present invention also includes a center divider that separates the fluid passages on the first pass of the light through the fluid and the second pass of the light through the fluid. This center divider blocks any undesired backscattered light and does not allow that light to reach the read optic. Our invention provides the ease of fiber optic packaging of a transflectance probe and the optical performance of a cross flow cell.

An object of our invention is to provide an improved transmission flow cell and method for photometric analysis of fluid flows with a minimal backscattered stray light and a well defined optical path length.

A further object of our invention is to provide a flow cell with a folded optical path that allows for compact, rugged packaging of the fiber optic cables.

The present invention improves on the known variations of fluid flow cells and fluid probes by offering co-located, collinear fiber optic ports and a center divider that eliminates backscattered light from reaching the detector.

Other objects, advantages and novel features of the present invention will become apparent from the following detailed description when considered in conjunction with the accompanying drawings and non-limiting examples herein.

DETAILED DESCRIPTION OF THE DRAWINGS

Figure 1:
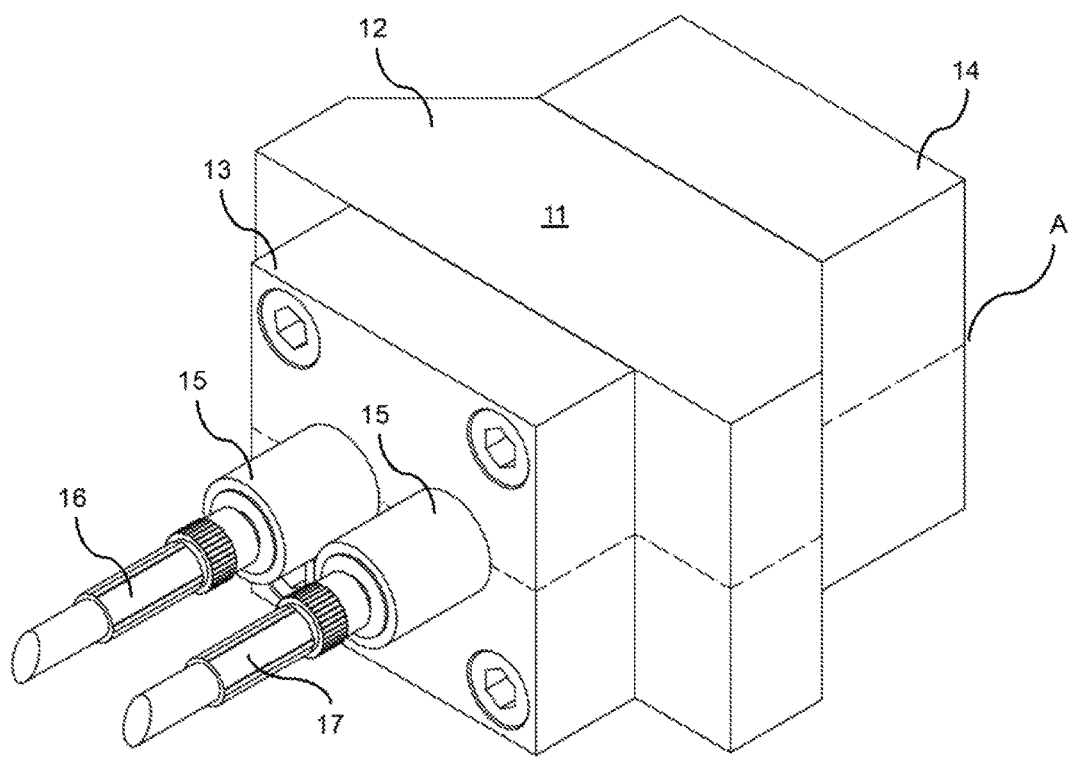
FIG. 1 is an isometric view of a flow cell assembly embodying the present invention.

Now referring to FIG. 1, the flow cell assembly designated generally by numeral 11 consists of a main body 12, an end cap 13 to mount two collimating lenses 15, and an end cap 14 to house reflecting optics. Fiber optic cables 16, 17 attach to each of the focusing/collimating lenses 15 and run from a light source and to a detector, respectively.

Figure 2:
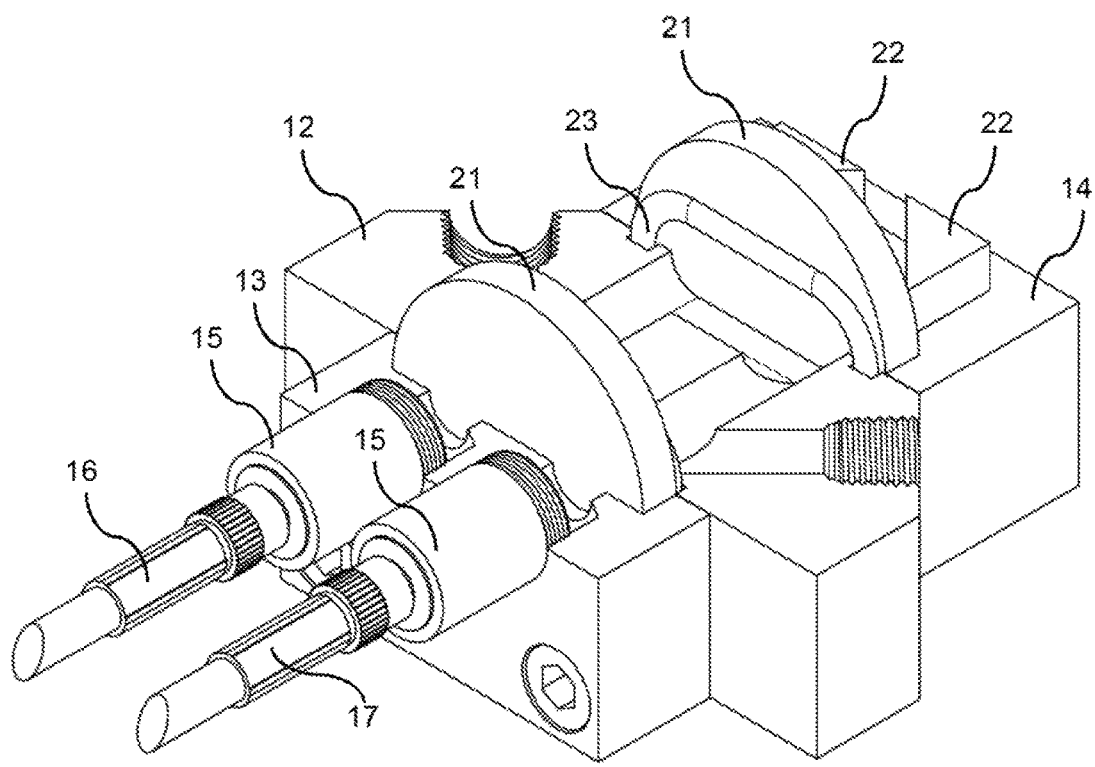
FIG. 2 is an isometric partial sectional view of our flow cell assembly where the flow cell body sectioned along the dashed lines A shown in FIG. 1 to illustrate the interior components.

FIG. 2 shows two optical windows 21, two right-angle prism mirrors 22 (only one being fully shown) and a window seal 23 that are located within the main body 12. In a currently preferred embodiment, the right-angle prism mirrors 22 have a broadband coating such as a dielectric coating which reflects light externally incident on the hypotenuse of each prism, and the windows have an antireflective coating such as a single-layer, dielectric coating with low reflectance at the wavelengths of interest.

Figure 3:
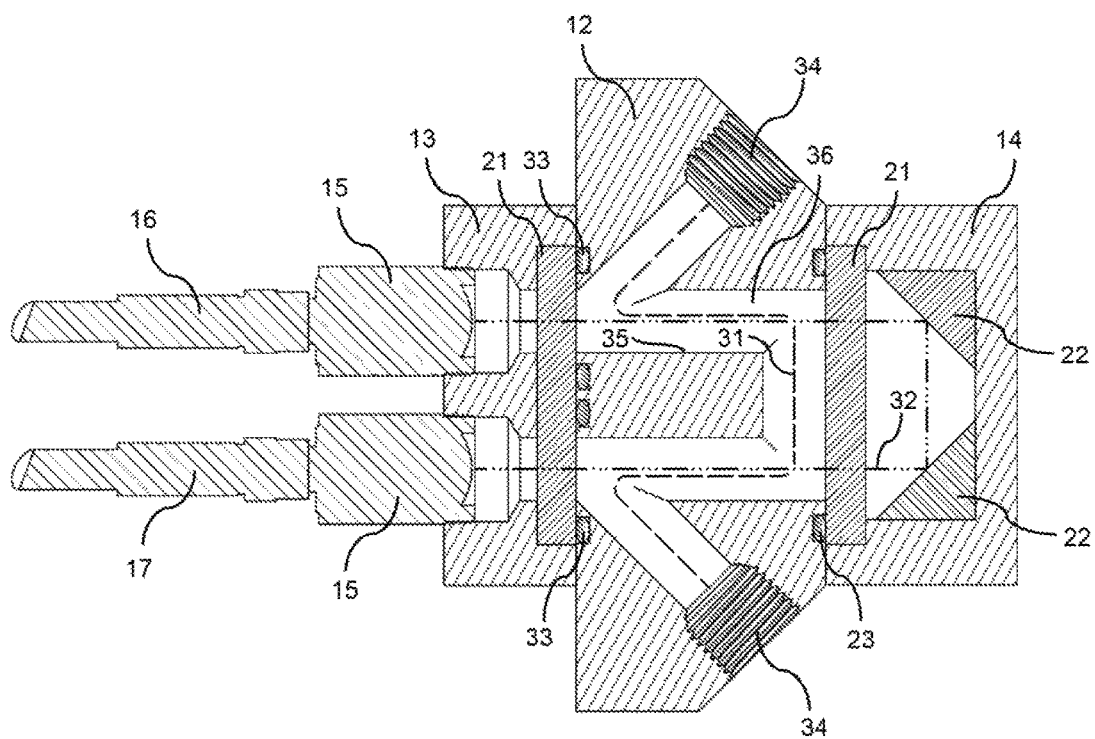
FIG. 3 is a cross-sectional top view of the flow cell assembly shown in FIGS. 1 and 2 depicting optical and fluid flow paths.
Figure 4:
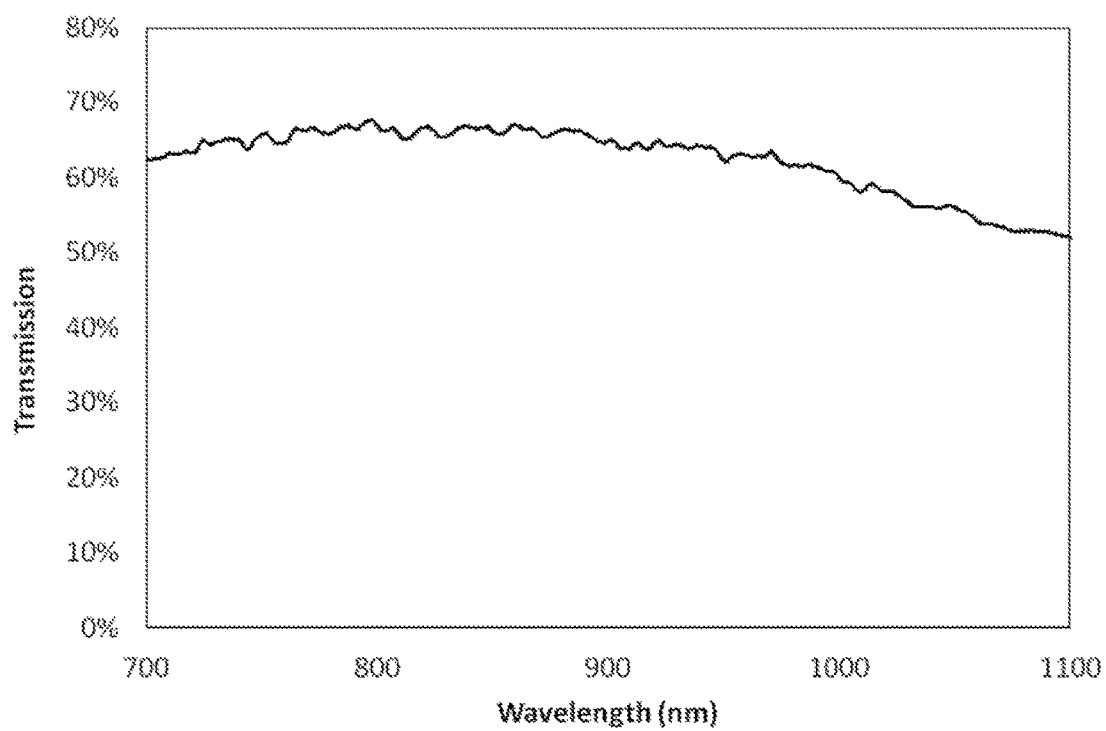
FIG. 4 is a graph showing the transmission losses in our flow cell as a function of light wavelength.
Figure 5:
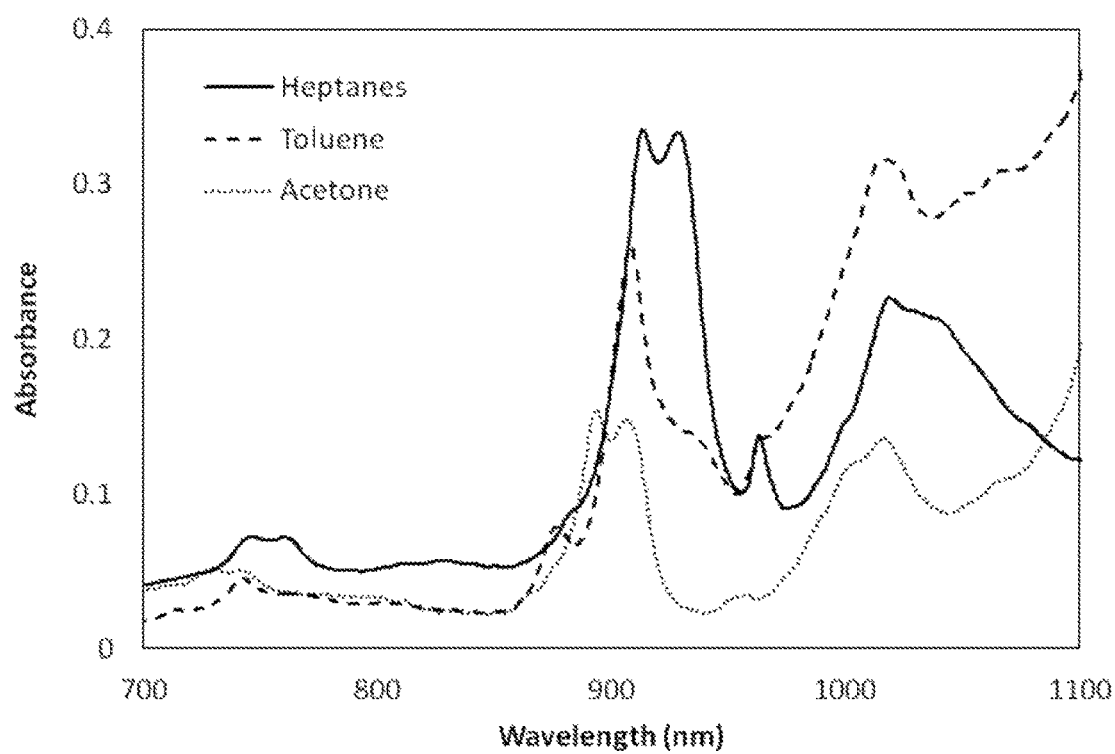
FIG. 5 is a graph showing the absorbance of several common chemicals in our flow cell as a function of the light wavelength.

FIG. 3 shows a full cross-sectional top view of the flow cell assembly 11 with a fluid flow path 31 depicted by dashed lines and an optical path 32 depicted by dash-triple-dot lines. The main body 12 contains a U-shaped fluid measurement cavity 36 with fluid entering and exiting at either tip of the "U" via cross-drilled inlet and outlet ports 34, depicted here as threaded features. The length of the "U" can be varied to accommodate the desired optical path length, which is defined as two times the distance between the windows 21. The fluid sample to be analyzed is pumped into the flow cell assembly 11 through one of the fluid ports 34, follows the depicted fluid path 31 and exits through the opposite fluid port 34. Direction of the fluid flow is inconsequential due to the symmetrical embodiment of the present invention. The fluid cavity is sealed against the optical windows 21 by two seals 33 on the optics end cap 13 side and a third seal 23 (see also FIG. 2) on the reflection end cap 14 side of the flow cell assembly 11 to protect the lenses and the turning mirrors from fluid contamination. Light emitted from a light source (not shown) is transmitted via one of the fiber optic cables 16 to a collimating lens 15, where the light is collimated into a beam with minimal divergence. The beam then passes through the first optical window 21, travels through the flowing fluid being measured, through a second optical window 21, is reflected off the hypotenuses of the two right-angle prism mirrors 22, passes back through the second optical window 21, travels back through the fluid, and passes back through the first optical window 21. The incident beam is then collected and refocused in a focusing lens and travels via the other fiber optic cable 17 to a spectrometer (not shown). A center divider 35 is provided in the main body 12 such light backscattered off the fluid or suspended particles cannot reach the read fiber. Discernment between the collimating and focusing lenses 15 is inconsequential due to the symmetrical configuration of the present invention.

In a currently preferred embodiment, the collimating/focusing lenses 15 use a piano-convex lens, and the illumination fiber has a smaller core diameter than the read fiber. The smaller illumination fiber more closely approximates a point source and leads to better collimation and less divergence in the cell. The larger read fiber allows for some divergence and provides for some small misalignment of the optics. In a preferred embodiment, the illumination fiber has a core diameter of about 100 micrometers, and the read fiber has a core diameter of about 400 micrometers.

Example 1—Measurement of Transmission Losses in Flow Cell

The transmission loss in our flow cell was measured for an empty flow cell containing no liquid. The transmission of light as a function of wavelength was measured with a spectrometer over the near infrared region of the electromagnetic spectrum. The transmission was also measured with the flow cell removed and a optical coupler placed between the end terminations of the fiber. Transmission was calculated at each wavelength by dividing the measured transmitted light through the flow cell by the transmitted light through the same optical circuit with the flow cell removed and expressing that quotient as a percentage. Together the lenses, windows, and mirrors provided for a transmission of 50 to 65%. As a point of reference, commonly cross flow cells without lenses has a transmission of only 10 to 20%.

Example 2—Measurement of Absorbance of Pure Compounds

Our flow cell was connected to the same spectrometer and light source described in Example 1. The flow cell was filled with isomers of heptane ("heptanes"), toluene, and acetone at different times. The transmission of light through the sample was used to calculate an absorbance. An empty flow cell was used to calculate the reference intensity for the purpose of calculating the absorbance. Peaks in the absorbance spectra correspond to spectral regions where the light is absorbed through interactions with the bonds in the molecules. In the a near infrared region the molar absorptivity is low compared to the more commonly probed mid-infrared region, requiring a longer pathlength. The path length used for these measurements was 5 cm. The spectra show clearly discernible spectral features and high signal-to-noise ratio.

Although we have shown and described several embodiments of our invention, we do not intend to be limited to the details thereof but intend to cover all changes and modifications encompassed by the scope of our appended claims.

We claim:

1. A flow cell for taking transmission measurements in a fluid, comprising a body having a substantially fluid measurement cavity having a bight portion and tip portions, co-linear fiber optic ports operatively arranged at one side of the body, fluid ports arranged at another portion of the body such that the fluid being measured enters at a first of the tip portions adjacent one of the fiber optic ports operative as an illumination port and exits at a second of the tip portions adjacent another of the fiber optic ports operative as a read port, a turning mirror system located adjacent the bight portion of the cavity, and a divider arranged in the cavity between the tip portions and configured to prevent light back-scattered off the fluid or off particles suspended in the fluid from reaching the read port.

2. The flow cell of claim 1, wherein the turning mirror system is comprised of a pair of right-angle prism mirrors.

3. The flow cell of claim 2, wherein the mirrors are provided with at least one of an anti-reflective coating and a broadband coating selected to reflect light externally incident on a hypotenuse of the prism mirrors.

4. The flow cell of claim 1, wherein a fiber optic cable is associated with each of the ports, and a collimating lens is arranged between each of the cables and the ports.

5. The flow cell of claim 4, wherein each collimating lens is a plano-convex lens.

6. The flow cell of claim 4, wherein the fiber optic cable associated with the port operative as the illumination port is selected to have a diameter smaller than the fiber optic cable associated with the port operative as the read port so that an illumination beam entering through the illumination port approximates a point collimated light source.

7. The flow cell of claim 4, wherein an optical window is operatively arranged between the lenses and the fluid ports.

8. The flow cell of claim 1, wherein an optical window is operatively arranged between the bight portion and the mirror system.

9. The flow cell of claim 8, wherein a second optical window is operatively arranged between the lenses and the fluid ports.

10. The flow cell of claim 9, wherein seals are provided between the optical windows and the body.

11. The flow cell of claim 1, wherein the mirror system includes an end cap operatively connected with the body.

12. The flow cell of claim 11, wherein an optical window is operatively arranged in the end cap between the bight portion and a pair of right-angle prism mirrors comprising the mirror system.

13. A method for taking measurements of a fluid, comprising flowing the fluid being measured into a fluid port of a flow cell body having a bight portion, tip portions and co-linear fiber optic ports operatively arranged at an end of the body such that the fluid being measured enters at a first of the tip portions adjacent a first of the fiber optic ports operative as one of an illumination port when a second of the fiber optic ports is operative as a read port or the read port when the second fiber optic port is operative as the illumination port, and flows toward a first location on the body at which a collimated beam is directed to travel through the fluid and be reflected off right-angle prism mirrors located adjacent the bight portion of the cavity to create incident light, having the fluid exit at another of the tip portions adjacent the second fiber optic port operative as one of the read port when the first fiber optic port is operative as the illumination port or the illumination port when the first fiber optic port is operative as the read port and directing the incident light to a second location adjacent the first location on the body via a substantially U-shaped path, wherein the collimated beam and incident light are divided at the bight portion to prevent back-scattered light or light reflected off fluid particles from reaching the second location.

14. The method of claim 13, wherein the collimated beam is directed to the body from a fiber optic cable through a focusing lens.

15. The method of claim 13, wherein the incident light is focused and transmitted through a fiber optic cable.

16. The method of claim 15, wherein the incident light is focused by a lens and then transmitted through a second fiber optic cable co-linear with the first-mentioned fiber optic cable.

17. A flow cell for taking transmission measurements in a fluid, comprising a body having a substantially fluid measurement cavity having a bight portion and tip portions, co-linear fiber optic ports operatively arranged at one side of the body, fluid ports arranged at another portion of the body such that the fluid being measured enters at a first of the tip portions adjacent a first of the fiber optic ports operative as one of an illumination port when a second of the fiber optic ports is operative as a read port or the read port when the second fiber optic port is operative as the illumination port and exits at a second of the tip portions adjacent the second fiber optic port operative as one of the read port when the first fiber optic port is operative as the illumination port or the illumination port when the first fiber optic port is operative as the read port, a turning mirror system located adjacent the bight portion of the cavity, and a divider arranged in the cavity between the tip portions and configured to prevent light back-scattered off the fluid or off particles suspended in the fluid from reaching the read port.

18. The flow cell of claim 17, wherein the turning mirror system is comprised of a pair of right-angle prism mirrors.

19. The flow cell of claim 18, wherein the mirrors are provided with at least one of an anti-reflective coating and a broadband coating selected to reflect light externally incident on a hypotenuse of the prism mirrors.

20. The flow cell of claim 17, wherein a fiber optic cable is associated with each of the ports, and a collimating lens is arranged between each of the cables and the ports.

* * * * *